United States Patent
Zeller (10) Patent No.: US 10,228,433 B2
(45) Date of Patent: Mar. 12, 2019

(54) PROCESSOR, MAGNETIC RESONANCE APPARATUS, AND METHOD FOR MEASUREMENT PLANNING OF A MAGNETIC RESONANCE MEASUREMENT SEQUENCE

(71) Applicant: Siemens Healthcare GmbH, Erlangen (DE)

(72) Inventor: Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 213 days.

(21) Appl. No.: 15/262,076

(22) Filed: Sep. 12, 2016

(65) Prior Publication Data

US 2017/0082710 A1 Mar. 23, 2017

(30) Foreign Application Priority Data

Sep. 18, 2015 (DE) .......................... 10 2015 218 001

(51) Int. Cl.
| G01R 33/54 | (2006.01) |
| A61B 5/055 | (2006.01) |
| G01R 33/28 | (2006.01) |

(52) U.S. Cl.
CPC ............ *G01R 33/543* (2013.01); *A61B 5/055* (2013.01); *G01R 33/288* (2013.01); *G01R 33/546* (2013.01)

(58) Field of Classification Search
CPC .......... G01R 33/20; G01V 3/32; A61B 5/055; G01N 24/00
USPC .......................... 324/200, 300, 301, 307, 309
See application file for complete search history.

(56) References Cited

U.S. PATENT DOCUMENTS

| 9,991,716 | B2* | 6/2018 | Cutright | H02J 3/383 |
| 9,992,855 | B2* | 6/2018 | Larroux | H05G 1/58 |
| 2010/0244829 | A1* | 9/2010 | Zenge | G01R 33/5635 324/309 |
| 2013/0090776 | A1 | 4/2013 | Feiweier | |
| 2015/0285885 | A1 | 10/2015 | Feiweier et al. | |
| 2016/0178714 | A1* | 6/2016 | Fautz | G01R 33/483 324/309 |
| 2017/0319097 | A1* | 11/2017 | Amthor | A61B 5/055 |
| 2018/0024214 | A1* | 1/2018 | Bhat | G01R 33/4828 324/309 |

* cited by examiner

Primary Examiner — Giovanni Astacio-Oquendo
(74) *Attorney, Agent, or Firm* — Schiff Hardin LLP (57) ABSTRACT

On the basis of a user interaction, values of measurement parameters of a magnetic resonance measurement sequence are established. A physical-technical limit value is computed for at least one selected measurement parameter.

18 Claims, 4 Drawing Sheets

PROCESSOR, MAGNETIC RESONANCE APPARATUS, AND METHOD FOR MEASUREMENT PLANNING OF A MAGNETIC RESONANCE MEASUREMENT SEQUENCE

BACKGROUND OF THE INVENTION

Field of the Invention

The invention concerns a computer for planning a magnetic resonance measurement sequence and a corresponding method, in particular using techniques for computing a physical-technical limit value of a selected measurement parameter of a set of measurement parameters of the magnetic resonance measurement sequence. The invention also concerns a magnetic resonance apparatus embodying such a processor.

Description of the Prior Art

In the planning of a magnetic resonance (MR) measurement sequence a user typically can change a large number of measurement parameters of a set of measurement parameters via an operating console. Various embodiments of user interfaces, such as a graphical user interface are known for performing this task.

As a result of the large number of measurement parameters of the set of measurement parameters it can be difficult for the user to plan a valid MR measurement sequence, i.e. to establish values for the different measurement parameters that fulfill specific physical-technical boundary conditions.

In addition situations can arise in which, for example as a result of parameter dependencies between different measurement parameters, making changes to a first measurement parameter influences the possibility of changing a second measurement parameter. This can mean that, as a result of the changes to the first measurement parameter, there must be renewed planning of the MR measurement sequence and many other different measurement parameters must be adapted accordingly. In this way the measurement planning becomes especially complicated.

Situations also can occur in which the effect of changing the first measurement parameter is that a valid value cannot be found for the second measurement parameter within the framework of the physical-technical boundary conditions. In such a case, a supporting routine (solve handler routine) can help in finding valid values for the measurement parameters of the set of measurement parameters. The execution of the solve handler routines can be processing-intensive and can require a certain amount of time. The measurement planning is thereby lengthened and carrying out the MR measurement sequence is delayed. If the user changes a value of a measurement parameter in the non-valid range, it takes a long time until a solution can be provided.

There is therefore a need for improved techniques for planning an MR measurement sequence. In particular a need exists for such techniques that at least remedy a few of the aforementioned disadvantages and restrictions of previously known techniques. In particular there is a need for techniques that make it possible to establish valid values for measurement parameters of a set of measurement parameters easily and rapidly within the framework of physical-technical boundary conditions.

SUMMARY OF THE INVENTION

In one aspect of the present invention, to a computer for the planning of an MR measurement sequence includes a user interface that is configured, on the basis of a user interaction, to establish values of measurement parameters of a set of measurement parameters of the MR measurement sequence. The computer further includes a processor that is configured, for at least one selected measurement parameter of the set of measurement parameters, to compute a physical-technical limit value. The computer further includes a data interface that is configured to transmit control signals between the computer and a sequence controller of a data acquisition scanner of the MR apparatus. The control signals indicate the values of the measurement parameters of the set of measurement parameters established on the basis of the user interaction.

For example, the at least one processor can be configured to control the user interface for carrying out the user interaction. The user interface can be implemented as hardware and/or software. For example, the user interface can be a graphical user interface (GUI). The user interface, as an alternative or in addition, can include voice control, a screen, a mouse, a keyboard, etc. Accordingly, the user interaction can be formed differently in different scenarios: It is possible for example, for the user interaction to include a number of user actions in the form of setting the values of the measurement parameters of the set of measurement parameters in the graphical user interface, for example by selection and definition by a cursor.

For example, the establishment of the values of the measurement parameters of the set of measurement parameters can be implemented on the basis of the user interaction, starting from reference values. The reference values can correspond to frequently used default values for a specific MR measurement sequence, which are stored in a pre-prepared database for example and/or are specific for a user profile of the user of the user interface. It is also possible for the reference values to be received by the computer from the MR apparatus within the framework of the control signals. Then, the user of the user interface, starting from these default values, can make changes until the (final) values are established, and these can be embodied in the control signals to the sequence controller of the MR apparatus.

These techniques can be applied in a versatile manner to a wide variety of forms and types of MR measurement sequences. For example, the inventive techniques can be applied to MR measurement sequences that are selected from the following group: FLASH, spin echo, turbo spin echo, gradient echo, image-accelerated techniques with undersampling of the k-space, Dixon-type measurement sequences, spectroscopy techniques, diffusion imaging, contrast-medium-supported measurement sequences, etc.

For example the measurement parameters of the set of measurement parameters can be selected from the following group: a measurement region in the read-out direction; a measurement region in the phase encoding direction; a slice thickness; a repetition time; an echo spacing; a spatial resolution in the read-out direction; a spatial resolution in the phase encoding direction; a partial Fourier factor, i.e. a factor that specifies whether only a part area of the k-space is sampled; an image acceleration factor for parallel imaging, i.e. a factor that specifies how large the proportion of k-space lines is that is not measured but will be reconstructed by parallel imaging methods such as SMASH, GRAPPA, SENSE, etc. for example; a bandwidth; a flow compensation mode, i.e. the selection of a method for flow compensation; a turbo factor for turbo spin echo imaging; a dimensionality of the imaging; a radio-frequency (RF) mode; a number of concatenations; a number of slices.

The physical-technical limit value for the at least one selected measurement parameter can thus mean: a restriction of the possible range of values for the value of the at least one selected measurement parameter, which results from physical and/or technical boundary conditions. In this case the limit value can comprise e.g. graduated restrictions, i.e. can differentiate between values for example that are possible without changes to values of further measurement parameters; values that are only possible with changes to further measurement parameters; and values that are not possible even with changes to further measurement parameters. The limit value can be defined for example in relation to discretized ranges of values of the selected at least one measurement parameter. It is possible for the limit value to define a range of values for example. It would be possible for the limit value to include a number of restrictions, e.g. a restriction toward low values and a restriction towards high values.

An example for a technical boundary condition is an operating specification of the MR apparatus. For example, the operating specification of the MR apparatus can be selected from the following group: a maximum field strength of gradient pulses; a maximum rate of change of gradient pulses; a maximum field strength of a gradient magnetic field for polarization of the magnetization; a maximum amplitude of RF pulses; a maximum RF power per unit of time, a maximum duration of the MR measurement sequence, etc.

The data interface can be implemented as hardware and/or software. In different scenarios the computer can be part of the MR apparatus. In such a case it is possible for the data interface to be an internal software protocol of the MR apparatus, which makes it possible to communicate between the at least one processor and the sequence controller of the MR apparatus. In other scenarios it is possible for the computer to be a separate physical unit and not to be integrated with the MR apparatus. Then it would be possible for the data interface to make possible communication between the computer and the MR apparatus via a transmission medium, which can be implemented as a wired and/or wireless medium.

Transmission of the control signals can be implemented, for example, by sending and/or receiving control signals through the data interface. The control signals, which indicate values of the measurement parameters established on the basis of the user interaction, can be transmitted, after conclusion of the measurement planning via the data interface to the MR apparatus. The measurement planning of the MR measurement sequence thus can take place in advance of the execution of the MR measurement sequence by the MR apparatus (i.e., the scanner thereof). For example, the control signals can initiate the execution of the MR measurement sequence. The sequence controller can be configured to control different components of the MR apparatus synchronized in time for carrying out the MR measurement sequence.

The computing of the physical-technical limit value allows the valid range of values for the at least one selected measurement parameter to be determined. It is thus possible to establish a valid set of measurement parameters rapidly on the basis of the user interaction. Incorrect inputs by the user, which make it necessary to trigger a supporting routine for finding a valid set of measurement parameters, can be avoided.

The processor can be configured to activate the user interface, so that the interface indicates the computed limit value to the user within the framework of the user interaction. In this way, it is possible for the user, before carrying out a user action within the framework of the user interaction for changing the value of the at least one measurement parameter, to be informed about the valid range. In this way, incorrect inputs that result in the establishment of the value outside the valid range can be avoided. The measurement planning thus can be carried out more rapidly.

It is possible for the processor to be configured to compute the limit value for the at least one selected measurement parameter prospectively before the establishment of the value of the at least one selected measurement parameter on the basis of the user interaction.

Such prospective computation can be, for example, computing the limit value before the user carries out a user action of the user interaction, from which e.g. the value of the at least one selected measurement parameter that will be transmitted within the framework of the control signal results.

The prospective computation can be triggered automatically. It is possible to preclude the prospective computation from being triggered by interaction by the user. For example, the prospective computation can be triggered autonomously by the starting of the measurement planning of the MR measurement sequence. A dedicated user interaction to initiate the prospective computation is not required.

In this way it is possible, such as within the framework of the user interaction, to indicate the physical-technical limit value and thereby prospectively prevent the user from selecting a value for the at least one selected measurement parameter outside the valid range of values.

For example, the processor can be configured to compute limit values of the at least one selected measurement parameter based on predetermined parameter dependencies between different measurement parameters of the set of measurement parameters and the at least one selected measurement parameter, as well as furthermore based on the values of the different measurement parameters of the set of measurement parameters established on the basis of the user interaction.

As an alternative or in addition, it is possible for the processor to be configured to compute the limit value of the at least one selected measurement parameter based on the predetermined parameter dependencies between the different measurement parameters of the set of measurement parameters and the at least one selected measurement parameter, as well as furthermore based on the reference values of the different measurement parameters of the set of measurement parameters.

In this way it can be insured that in each case current values are taken into account in the computation of the limit value of the at least one selected parameter, as they are currently active in the user interaction.

The parameter dependencies can refer to physical dependencies existing between the measurement parameters that have the effect that changing a first measurement parameter of the set of measurement parameters also results in a change of a second measurement parameter of the set of measurement parameters, which is different from the first measurement parameter. As an alternative or in addition the parameter dependencies can refer to physical dependencies that have the effect that changing a first measurement parameter of the set of measurement parameters also results in a change of the limit value of the second measurement parameter.

The parameter dependencies can be selected for the following group: the measurement range in the read-out direction—the spatial resolution in the read-out direction—the echo spacing; and the spatial resolution in the phase encoding direction—the partial Fourier factor—the image acceleration factor for the parallel imaging—the turbo factor for turbo spin echo imaging; and the repetition time—the number of concatenations. A further example for parameter dependencies is all measurement parameters that influence the time sequence of the MR measurement sequence, i.e. for example the number of slices, the resolution in the read-out direction, the resolution in the phase encoding direction, the image acceleration factor for the parallel imaging, the partial Fourier factor, the flow compensation mode, the turbo factor, the dimensionality of the imaging, the RF mode/gradient mode, the slice thickness, etc. have an influence on the repetition time and/or the echo spacing, depending on the type of MR measurement sequence.

By taking account of the parameter dependencies during computation of the limit value, complicated relationships between the different measurement parameters of the set of measurement parameters can be taken into account; it is possible to design the effects of changing the value of a first measurement parameter on the valid range of values of a second measurement parameter more transparently.

The at least one processor can be configured to establish a further limit value of the at least one selected measurement parameter based on the predetermined parameter dependencies between the different measurement parameters of the set of measurement parameters and the at least one selected measurement parameter, as well as further based on anticipated values of the different measurement parameters of the set of measurement parameters. The values of the different measurement parameters established on the basis of the user interaction can be at least partly different from the anticipated values of the different measurement parameters.

Through the use of anticipated values of the different measurement parameters the further limit value can thus be computed in respect of an anticipated user action. The further limit value thus cannot be computed based on current values for the measurement parameters of the set of measurement parameters, but instead is computed for values that might possibly be established by the user within the framework of the user interaction by a corresponding user action. This can allow, as soon as the anticipated value is actually established on the basis of the user interaction, the limit value for the at least one selected measurement parameter to be made available especially rapidly and with a low latency time. A renewed computation is then not necessary.

In general, a wide variety of techniques and approaches can be used to determine the at least one selected measurement parameter of the set of measurement parameters for which the limit value is to be computed. In one scenario the limit value can be computed for all measurement parameters. In general the computation of the limit value can take some time because of the computing capacity required. Therefore it can be worth making the effort to select such measurement parameters for computing the associated limit values that have a greater relevance—for example in relation to possible incorrect inputs outside the valid range of values and/or have a frequency of establishing the corresponding value on the basis of the user interaction by the user. It is also possible to select a number of measurement parameters for computing the associated limit value. For example a number of measurement parameters can be selected in a specific order with which the computation of the associated limit value is processed—in this case the order can again be determined based on the relevance, as described above.

For example the at least one measurement parameter can be selected from the set of measurement parameters based on a user action of the user of the user interface within the framework of the user interaction. For example, within the framework of the user interaction, one or more measurement parameters can be selected from the set of measurement parameters for computing the limit value.

The user action can indicate that the at least one selected measurement parameter has an especially significant relevance in relation to the computation of the associated limit value. For example, the user action could be selection of a logical grouping of measurement parameters in the graphical user interface of the user interface by the user within the framework of the user interaction. In this case the logical grouping can include the at least one measurement parameter. In this case the logical grouping can correspond to a card or tab of a menu structure of the graphical user interface for example. For example, the user can promptly set or establish the value of the at least one selected measurement parameter on the basis of the user interaction, if the corresponding logical grouping or the corresponding tab has been activated previously. In such a scenario the computation of the corresponding limit value can be especially relevant.

As an alternative or in addition, the user action can be establishing the value of a further measurement parameter of the set of measurement parameters on the basis of the user interaction. Such measurement parameters can be selected from the set of measurement parameters for computation of the limit value as are influenced as a result of the parameter dependencies by the further measurement parameter. In such a scenario it can be assumed that the limit value has changed because of the change of the value of the further measurement parameter; then the computation of the corresponding (updated) limit value can be especially relevant.

It is also be possible for the at least one processor to be configured to select the at least one selected measurement parameter from the set of measurement parameters based on a user profile of a user of the user interface.

For example, the user profile of the user can indicate those measurement parameters of the set of measurement parameters for which the user has in the past established values that deviate from the reference values especially frequently within the framework of the user interaction. The user profile of the user can indicate those measurement parameters of the set of measurement parameters for which the user has in the past established values that lie outside the valid range of values especially frequently within the framework of the user interaction. The user profile of the user can indicate those measurement parameters of the set of measurement parameters for which in the past the different users of the MR apparatus have established values especially frequently that differ from the reference values. The user profile of the user can indicate those measurement parameters of the set of measurement parameters for which in the past the user has especially frequently carried out a user action within the framework of the user interaction. In the different examples illustrated here for the user profile it is possible that the respective information is stored specifically for different people being examined. Thus, depending on the person being examined for whom the measurement planning is undertaken, another measurement parameter can be selected for computation of the limit value.

As an alternative or in addition, the processor can be configured to select the at least one selected measurement parameter from the set of measurement parameters based on a profile of a person being examined, for whom the measurement planning is carried out. The person being examined can be indicated by the user interface or in another way. For example, one or more measurement plannings may already have been performed in the past for the examination subject or magnetic resonance measurement sequences for the imaging of the person being examined have been carried out. It is possible for the profile to indicate the corresponding magnetic resonance measurement sequence and/or indicates measurement parameters or values of measurement parameters that were used. In this way it can be possible to draw a conclusion about values of measurement parameters highly likely to have been selected.

By such techniques, the measurement parameters that are selected from the set of measurement parameters for computation of the associated limit value are those that have an especially great relevance for the respective user of the MR apparatus. The computation of the limit values for the different selected measurement parameters thus can be undertaken user-specifically.

It is also be possible for the processor to be configured to select the at least one measurement parameter from the set of measurement parameters based on a computing power required for computation of the limit value.

The computing power can be quantified, for example, by a time duration required for computing the corresponding limit value. As an alternative or in addition, the computer power can be quantified by a number of computing steps that are needed in order to compute the corresponding limit value. For example, the respective associated required computing power can be stored in a database for the different measurement parameters of the set of measurement parameters. The different entries of the database can be updated in each case after the computation of a limit value based on the then measured required computing power. For example, the measurement parameters can be selected from only the set of measurement parameters for computation of the limit value that require a high computing power for computation of the limit value. It is thus possible for especially computing-intensive computation of limit values to be carried out prospectively, so that, at a point in time at which the corresponding limit value is of especially great relevance for the user, the computation has already been done and the limit value can be made available with a short latency time.

For example, the processor can be configured to control the user interface on a first thread. The processor can also be configured to compute the limit value of the at least one selected measurement parameter on a second thread. The processor can be configured to execute the first thread with a higher priority than the second thread.

In this way, the computation of the limit values can be implemented in the background. For example, the processor can be configured for multitasking. It is then possible to use lower-priority processes of multitasking for the computation of the limit values. In this way, high-priority processes, such as the controlling of the user interface for carrying out the user interaction, are not delayed by the computation of the limit values.

With this embodiment, even the computing-intensive computation of limit values for the at least one measurement parameter does not influence, or does not significantly influence, the remaining operation of the processing. At the same time, the information about the limit value is available without any significant delay, if this is of relevance.

The computer can include a memory to store data that are indicative for the computed limit value, and data that are indicative for the values of the measurement parameter of the set of measurement parameters established on the basis of the user interaction in the memory.

In a simple scenario, the data that are indicative for the computed limit value can include the limit value itself. Accordingly it is possible in a simple scenario for the data that are indicative for the values of the measurement parameters of the set of measurement parameters established on the basis of the user interaction to include the values of the measurement parameters themselves. In other scenarios it is possible for the data to be derived variables.

For example, data can be stored for those values of the measurement parameters that are established especially frequently by a user of the user interface. Then a renewed computation of the limit values at a later point in time—at which the same values of the measurement parameters are established—may no longer be required, or required only to a restricted extent.

The data that are indicative for values of the measurement parameters of the set of measurement parameters established on the basis of the user interaction, can be a hash total that includes the values of the measurement parameters of the set of measurement parameters established on the basis of the user interaction. For example, the hash total can unambiguously indicate the established values of the measurement parameters of the set of measurement parameters. It is not necessary for the hash total to be established by an injective function from the values of the measurement parameters of the set of measurement parameters. In this way, it is possible for fewer data to have to be stored in the memory so a smaller memory can be used.

The invention also concern an MR apparatus that has an MR data acquisition scanner with a gradient system and an RF transmit/receive system. The MR apparatus further includes the computer according to the present invention, as described above. The MR apparatus further includes the sequence controller. The sequence controller is configured to control the gradient system and the RF transmit/receive system based on the control signal for carrying out the MR measurement sequence.

Such an MR apparatus achieves the same advantages achieved by the computer, as described above.

The present invention also concerns a method for planning of an MR measurement sequence. The method includes the establishment of values of measurement parameters of a set of measurement parameters of the MR measurement sequence in a computer by a user interaction with a user interface. The method further includes, for at least one selected measurement parameter of the set of measurement parameters, computation of a physical-technical limit values and the transmission of control signals that designate the values of the measurement parameters of the set of measurement parameters of MR measurement sequence established on the basis of the user interaction.

For example the method can be executed by the computer in accordance with the invention.

The method in accordance with the invention achieves the advantages achieved by the computer in accordance with the invention, as described above.

The present invention also encompasses a non-transitory, computer-readable data storage medium encoded with programming instructions (program code), that can be loaded into a control and evaluation computer of a magnetic resonance apparatus. The programming instructions cause the control and evaluation computer to operate as described above in accordance with the present invention, when those instructions are executed by the control and evaluation computer. As described above, the programming instructions can be executed by a single computer or processor, or can be distributed among multiple individual processors that are in communication with each other.

The features described above and features that will be described below can be used not only in the corresponding explicitly stated combinations, but also in further combinations or in isolation, without departing from the scope of the present invention.

DESCRIPTION OF THE PREFERRED EMBODIMENTS

The present invention will be explained in detail below on the basis of preferred exemplary embodiments, which refer to the drawings. In the figures the same reference characters designate the same or similar elements. The figures are schematic representations of different forms of embodiment of the invention. Elements shown in the figures are not necessarily shown true-to-scale. Instead the different elements shown in the figures are reproduced such that their function and general purpose are able to be understood by the person skilled in the art. Connections and couplings between functional units shown in the figures can also be implemented as an indirect connection or coupling. A connection or coupling can be implemented by wire or wirelessly. Functional units can be implemented as hardware, software or a combination of hardware and software.

The invention relates to techniques for computation of a physical-technical limit value for at least one measurement parameter that is selected from a set of measurement parameters of an MR measurement sequence. Through this a user can be supported during the process of establishing values for the measurement parameters of the set of measurement parameters that lie within a valid measurement range; this enables the measurement planning of the MR measurement sequence to be carried out in a targeted and efficient manner.

It is thereby possible for the limit value to be indicated within the framework of a user interaction, on the basis of which the user establishes values of measurement parameters of the set of measurement parameters—for example by a corresponding graphical output. In particular it can be possible for the limit value already to be indicated at a point in time at which the user by a user action has selected a specific measurement parameter, but still before the user changes or finally establishes the value of the selected measurement parameter by a further user action. The limit value thus can be computed prospectively, i.e. before the establishment of the value of the at least one selected measurement parameter on the basis of the user interaction. For example the limit value could be computed as soon as the user selects a tab that includes the at least one selected measurement parameter, in a graphical user interface.

Figure 1:
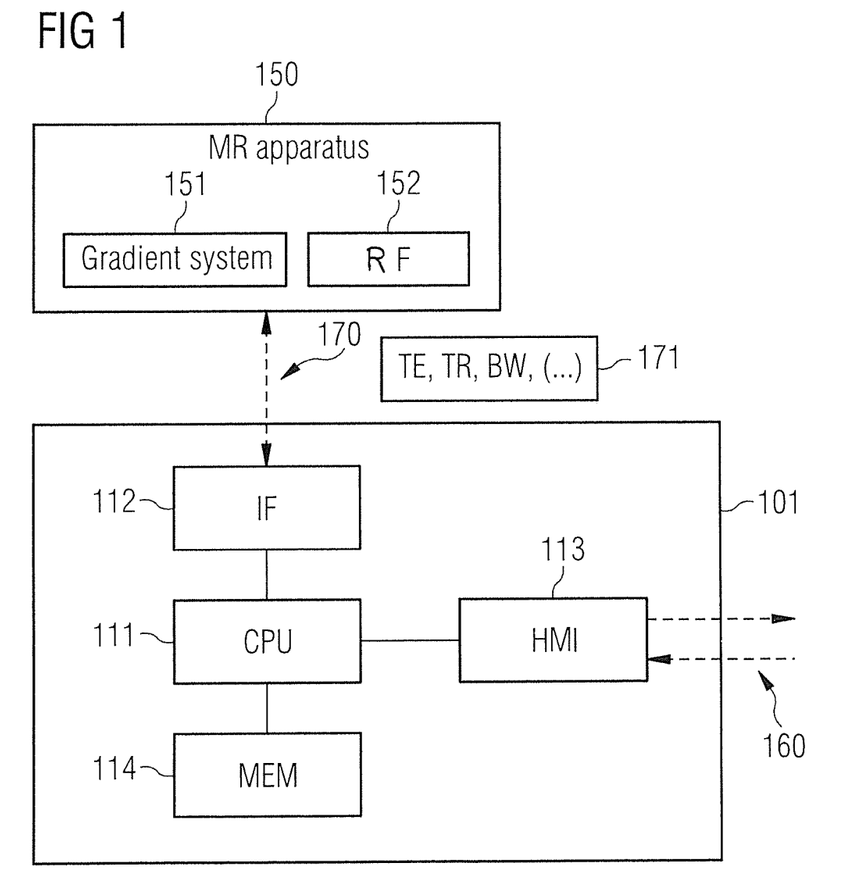
FIG. 1 schematically illustrates a computer in accordance with the present invention, configured to transmit control signals to an MR apparatus that indicate values of measurement parameters of a set of measurement parameters of an MR measurement sequence established on the basis of a user interaction.

FIG. 1 schematically illustrates a computer 101 that is configured to implement corresponding techniques. The computer comprises a processor 111. For example the processor 111 can be a multicore processor. In particular the processor 111 can be configured to execute computations in parallel or quasi in parallel on a number of threads. The processor can thus be configured to process different tasks within the framework of multiprocessor operation.

The processor 111 is coupled to a memory 114, for example a non-volatile memory such as ROM or RAM. The memory 114 can store program code that can be executed by the processor 111. The effect of execution of the program code from the memory 114 by the processor 111 can be that the processor 111 carries out techniques for computation of a physical-technical limit values for at least one measurement parameter of a set of measurement parameters of an MR measurement sequence.

In this context the processor 111 communicates via a data interface 112 with an MR apparatus 150. The processor 111 sends control signals 171 for example via the data interface 112 to an MR data acquisition scanner of the MR scanner 150, which has a gradient system 151 and an RF transmit/receive system 152.

The control signals 171 indicate values of measurement parameters of a set of measurement parameters of an MR measurement sequence established on the basis of a user interaction 160. The effect of the control signals 171 is that the scanner carries out the MR measurement sequence with the indicated values of the measurement parameters. For example the gradient system 151 can be configured to apply a time sequence of gradient pulses; the gradient pulses can modify the phase of the magnetization of the nuclear resonance. The RF transmit/receive system 152 can be configured to radiate RF pulses within the framework of the MR measurement sequence and to detect signals of the relaxing magnetization as raw data entered in the k-space.

FIG. 1 shows a scenario in which the MR apparatus 150 and the computer 101 are embodied as separate units. In this scenario the MR apparatus 150 and the computer 101 are coupled via a data connection 170; for example the data connection could be implemented via a wired or wireless transmission medium. In other scenarios it would also be possible for the MR apparatus 150 and the computer 101 to be embodied as a single unit. In particular in such a scenario it is possible for the data interface 112 to be predominantly implemented as software and for the data connection 170 to be an internal communication protocol for example.

The computer 101 further has a user interface 113. The user interface 113 is configured to carry out the user interaction 160. The user interface 113 could further be configured for example to output measurement data of the magnetic resonance measurement sequence and/or of other measurement sequences, for example respiration belt signals or ECG signals, to the user. The processor 111 can control the user interface 113 accordingly. The user interface 113 can include one or more of the following elements: a graphical user interface; a display facility; a keyboard; a mouse; a voice control. Within the framework of the user interaction 160 the user can undertake a number of user actions for example.

Figure 2:
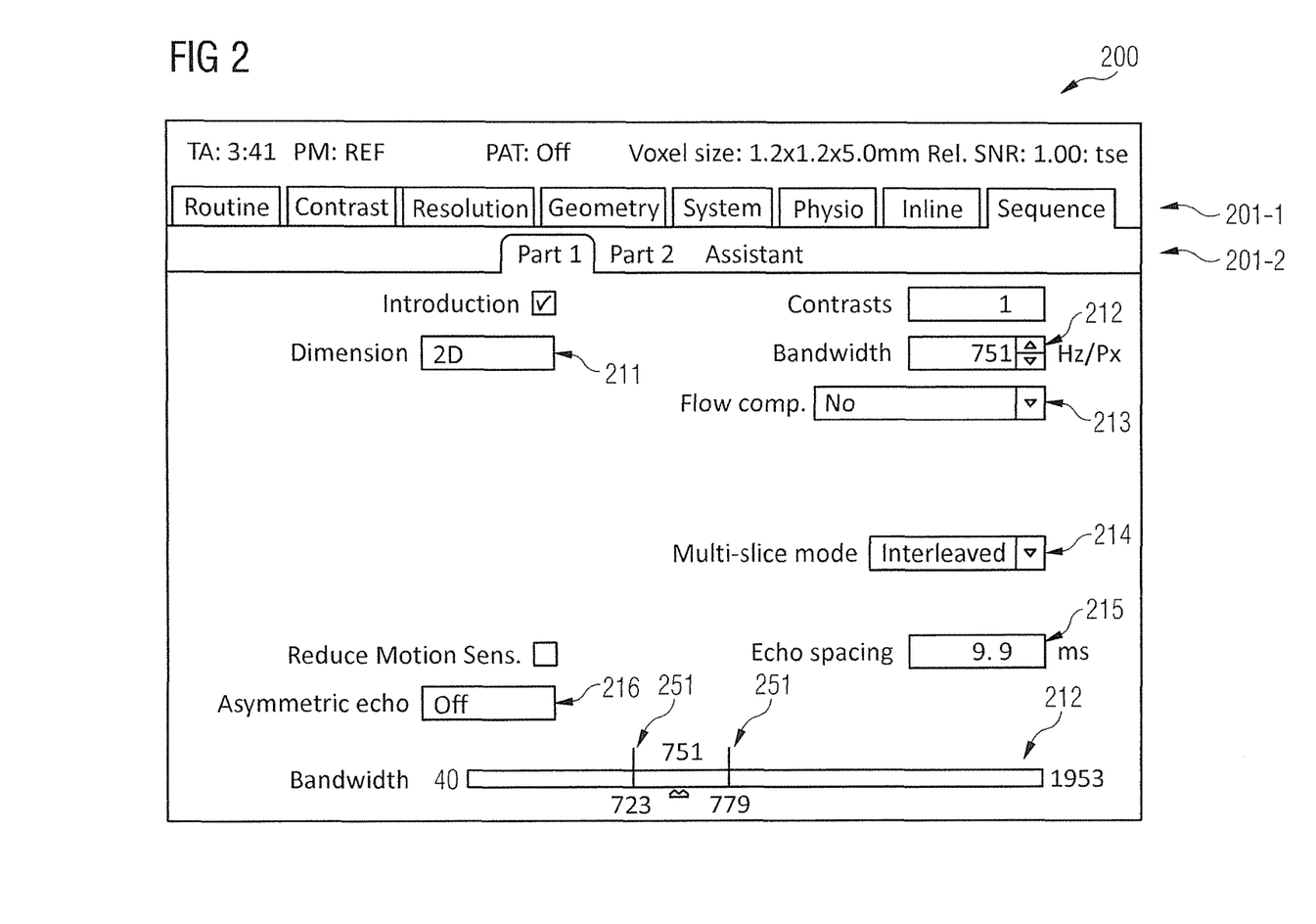
FIG. 2 illustrates a user interface of the computer in accordance with FIG. 1 that is configured to carry out the user interaction, wherein the user interface is a graphical user interface that makes it possible to establish values of the measurement parameters of the set of measurement parameters of the MR measurement sequence by user actions, wherein the graphical user interface further indicates physical-technical limit values for a selected measurement parameter of the set of measurement parameters within the framework of the user interaction.

FIG. 2 illustrates a graphical user interface 200 in greater detail. The graphical user interface 200 has a number of tabs 201-1, 201-2, which implement a logical grouping of measurement parameters 211-216. In the example of FIG. 2 a specific tab 201-1, 201-2 is activated, through which it is made possible for the user to change values for the dimensionality 211, the bandwidth 212, the flow compensation mode 213, the multi-slice mode 214, the echo spacing 215 and the asymmetric echo 216 as measurement parameters by a corresponding user action and establish them for the MR measurement sequence. Through different user actions within the framework of the user interaction 160 the user can thus change the values of the different measurement parameters 211-216 and thus establish the values that can be sent within the framework of the control signals 171 to the MR apparatus 150 via the data interface 112.

The user interface 200 can be initialized with specific reference values for the different measurement parameters 211-216. The reference values can be held in a database, which is stored in the memory 114 for example; for example the database could be user-specific for a user of the user interface 113.

As soon as the user selects the corresponding tab 201-1, 201-2 within the framework of a corresponding user action, the bandwidth 212 is selected as measurement parameter, for which the corresponding limit value 251 is to be calculated. Depending on available computing capacity, shortly after the user action in the form of selecting the corresponding tab 201-1, 201-2, the corresponding limit value 251 can therefore already have been computed, e.g. a few seconds after the selection of the corresponding tab 201-1, 201-2. The computation of the limit value 251 thus can be done prospectively before the establishment of the value for the bandwidth 212 by the user within the framework of the user interaction 160 by a corresponding further user action.

In order to compute such limit values 251 of measurement parameters 211-217 that are of great relevance for the user as promptly as possible, different strategies can be followed for selecting the measurement parameters 211-217, for which the limit value 251 is to be computed. For example the required computing power could be taken into account when selecting the measurement parameters 211-217 for computation of the limit value 251. Those measurement parameters 211-216 are preferably selected that require an especially high or low computing power for computation of the associated limit values 251. In further scenarios it would be possible for example for those measurement parameters 211-217 to be selected from the set of measurement parameters for which a user profile of the user of the user interface 113 indicates that they are of particular relevance for the user. The user profile can, for example, indicate a frequency with which the user values of the different measurement parameters 211-216 changes in relation to the reference values; then it can assumed in particular the measurement parameters 211-216 that are of great relevance are those in which frequently a user action brings about a change of the associated values. Such a preference can also be predetermined by a manufacturer of the MR apparatus 150. An example would be that typically the measurement range is changed more frequently by a user action by the user than the flow compensation mode. The selection of the different measurement parameters for computation of the associated limit values 251 can be a sequence with which the associated limit values 251 for the selected measurement parameters 211-216 will be computed. Such measurement parameters, which have a higher relevance for the user, can be prioritized in the sequence, so that the associated limit value 251 will be computed earlier. By such and further techniques, the limit value 251 for relevant measurement parameters 211-217 can be computed especially rapidly and with low latency time.

As soon as the limit value 251 is computed, the limit value 251 for the corresponding measurement parameters 212 is indicated within the framework of the user interaction 160; in FIG. 2 an implementation is shown in which in the graphical user interface 200 the limit value 251 is shown in the form of a bar. In this way the user is guided in establishing a value for the bandwidth 212, which lies within the valid range of values, through the user interaction 160.

A wide variety of techniques for indicating the limit value 251 within the framework of the user interaction 160 can be implemented. For example, especially for quasi-continuous measurement parameters, the limit value 251 can be illustrated as a color graduation; for a value of the measurement parameters 211-216, which lies within the valid range could be indicated with a green color; red could indicate a value of the corresponding measurement parameter 211-216, which lies outside the valid range of values, but for which possibly within the framework of a supporting routine, for example by modification of values of other measurement parameters 211-216, a valid set of measurement parameters can be found. Gray could accordingly indicate a value of the corresponding measurement parameter 211-216, for which basically no valid set of measurement parameters can be found any longer. A further technique for indicating the limit value 251 could for example include that, for the selection of values from pre-determined options (cf. FIG. 2: flow compensation mode 213), such values as lie outside the valid range of values will be shown as options in pointed brackets.

A very wide variety of techniques can be employed for computation of the limit value 251. In a simple implementation the limit value 251 is computed on the basis of an operating specification of the MR apparatus 150. In such a scenario it can be unnecessary or can only be necessary to a limited extent to take account of current values of further measurement parameters 211-216 in the computation of the limit value 251. The limit value 251 can then be computed especially quickly.

Figure 3:
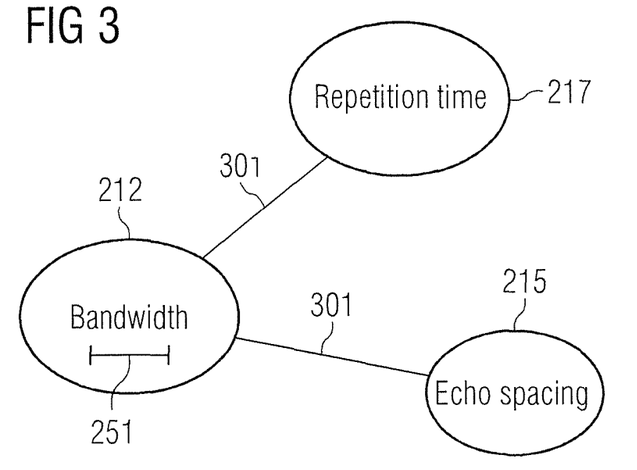
FIG. 3 schematically illustrates parameter dependencies between different measurement parameters of the set of measurement parameters of the MR measurement sequence.

In other scenarios parameter dependencies 301 (cf. FIG. 3) between different measurement parameters 212, 215, 217 can also be taken into consideration when computing the limit value 251. In the example of FIG. 3 the limit value 251 of the measurement parameter of the bandwidth 212 depends for example on the values of the repetition time 217 and the echo spacing 215.

For example, as soon as the value of one of the measurement parameters 215, 217 is changed or established within the framework of the user interaction 160, the bandwidth 212 for computing the associated limit values 251 can be selected; to this extent the changing of the value of the repetition time 217 and/or of the echo spacing 215 can have the effect that the limit value 251 for the bandwidth 212 is computed (again). In this way it can be achieved that there is always a current limit value 251—matched to the current active values of the further measurement parameters 211-217—is present. Thus in this case the current values of the repetition time 217 and the echo spacing 215 active in the user interface 200 during computation of the limit value 251 of the bandwidth 212 are taken into account during computation. Thus basically the reference values and values already changed by the user by a user action, i.e. values of the different measurement parameters 211-217, for the different measurement parameters 211-217, which have a parameter dependency 301 with the bandwidth 212 established on the basis of the user interaction 160 are taken into account.

Furthermore, anticipated values of the different measurement parameters 211-217 of the set of measurement parameters 171, which have a parameter dependency 301 with the bandwidth 212 can be taken into account for example during computation of the limit value 251 or of a further limit value for the bandwidth 212. The anticipated values can be different from the reference values and the values already changed by the user, i.e. different from the values established on the basis of the user interaction 160. For the anticipated values it can be assumed with a certain probability that these will be selected or established by the user within the framework of the user interaction 160 by user action in the future.

Various techniques are conceivable for determining the anticipated values. The anticipated values can for example be especially frequently used historically. The anticipated values can correspond to MR measurement sequences that have already been carried out by the MR apparatus 150 and that allow certain conclusions to be drawn for the present MR measurement sequence. For example, within the framework of an MR measurement sequence already carried out for imaging of an abdomen of a person being examined, a measurement range of 450 mm can have been established; it can then be assumed with a specific probability, that also in the present MR measurement sequence the measurement parameters of the measurement ranges will be set to 450 mm. When the user then actually establishes the anticipated values within the framework of the user interaction 160, the limit value 251 can be indicated especially rapidly.

Accordingly it is possible to compute limit values 251 for different measurement parameters 211-217 not only for the MR measurement sequence activated within the framework of the user interaction 160, but also for further MR measurement sequences, that are already located in a corresponding queue for example, but for which the measurement planning is still outstanding. However it would also be possible to compute the limit values 251 for the measurement parameters 211-217 for MR measurement sequences that are not yet in the corresponding queue, but for which it appears apparent that they will be planned and carried out in the future by the user. Such a decision can be made based for example on earlier comparable examinations of the person being examined. In different variants it is also possible for the limit values 251 for the measurement parameters 211-217 for all, especially frequently executed MR measurement sequences in the entire examination database; such a computation can especially be independent of the person currently being examined.

A few or all computed limit values 251 can be stored in the memory 114 for example; in particular the stored limit values 251 are stored in relation to a set of values of the different measurement parameters 211-217, for which the limit values 251 are valid and have been computed. This means that data that are indicative for the computed limit value 251, and data that is indicative for values of the measurement parameters 211-217 of the set of measurement parameters established on the basis of the user interaction 160, can be stored in the memory 114. In this way it is possible to indicate the corresponding limit values 251 especially rapidly and without latency time, if values for the different measurement parameters 211-217 are active, for which the limit value 251 have already been computed. There does not have to be any re-calculation.

Since in this context typically e.g. only three states (impossible, possible without changes to further measurement parameters 211-217, possible with changes to further measurement parameters 211-217) have to be stored for the different values within the range of values of a measurement parameter 211-217, the amount of data typically having to be stored is comparatively limited. It is also possible to reduce the amount of data to be stored in relation to the data that is indicative for the values of the measurement parameters 211-217 established on the basis of the user interaction 160. For example a corresponding range of dispersion sum could be stored. The range of dispersion sum can be created by the values of all relevant measurement parameters 211-217 being taken into account.

Figure 4:
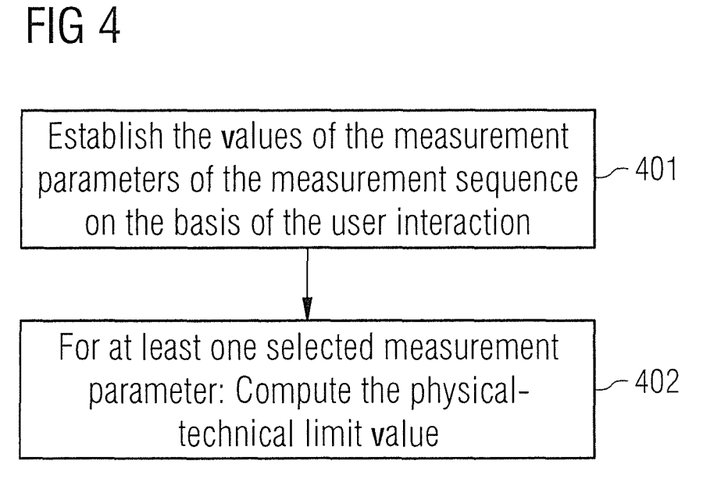
FIG. 4 is a flowchart of an embodiment of the method in accordance with the invention.

FIG. 4 is a flowchart of a method in accordance with different forms of execution of the present invention. The method in accordance with FIG. 4 can be executed by the processor 100.

The values of the measurement parameters 211-217 of the MR measurement sequence are established on the basis of the user interaction 160, 401.

The limit values 251, 402 are computed for at least one selected measurement parameter 211-217.

For example the steps 401, 402 can be executed in parallel. To this end the processor 111 could use different threads for controlling the user interface 113 on the one hand and for computation of the limit value 251 for the at least one selected measurement parameter 211-217 on the other hand. In particular it would be possible for example for step 402 to be executed with a lower priority than step 401.

The user interface 113 for executing the user interaction 160 can be controlled on one thread. As an alternative or in addition it would also be possible to control the user interface for displaying measurement data of a further measurement sequence that has already been initiated for the person being examined and e.g. could relate to ECG or respiration belt signals.

Figure 5:
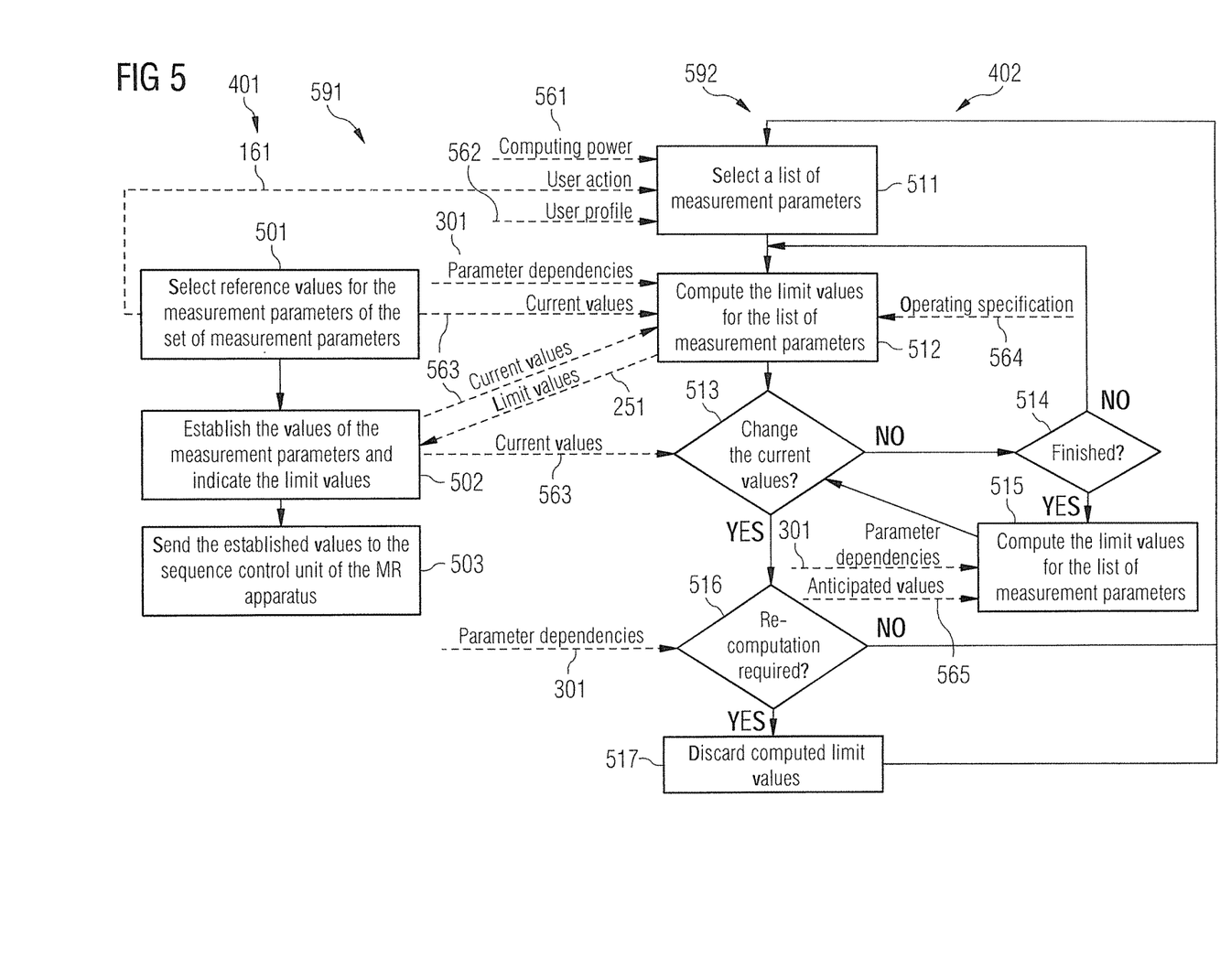
FIG. 5 is a flowchart of another embodiment of the method in accordance with the invention.

FIG. 5 illustrates different aspects in relation to the parallel execution of steps 401, 402. In this case details for step 401, which are executed on a first thread 591, are shown on the left in FIG. 5. Details for step 402, which are executed on a second thread 592, are shown on the right in FIG. 5.

In 501 reference values for the measurement parameters 211-217 are selected; for example the reference values can be obtained from a database that is held in the memory 114. The user interaction 160 is adapted accordingly; for example the graphical user interface 200 could be initialized with the reference values.

Then, in 502, the values of the measurement parameters 211-217 are established within the framework of the user interaction 160. In this step the different limit values 251 are indicated, which have each been computed 512 previously for current active values 563 of the measurement parameters 211-217. As soon as the measurement planning is ended, the values of the measurement parameters 211-217 established in this way are sent 503 to the MR apparatus 150 by means of the control signals 171.

In order to insure that valid limit values 251 are indicated in each case, the current active values 563 are transmitted in each case from the first thread 591 to the second thread 592.

Within the framework of the second thread 592 initially a list of measurement parameters 211-217 is selected 511 from the set of measurement parameters, for which subsequently in the corresponding sequence of the list the respective limit value 251 will be computed, 512. On selection of the different measurement parameters 211-217 in particular the required computing power 561, the user profile 562, and a user action 161 can be taken into account. For example the measurement parameters 211-217 could be selected as a function of a user action 161, which indicates that the user has activated a specific tab 201-1, 201-2. On selection of the different measurement parameters 211-217, especially relevant measurement parameters 211-217 could also be prioritized for den the user, wherein the relevance can be indicated for example by a frequency of the activation within the framework of the user profile 562. Also those measurement parameters 211-217 can be selected, for which the computation of the respective associated limit value 251 is especially computing-intensive.

The computation of the limit values 251 takes account of operating specification 564 of the MR apparatus 150. In addition the parameter dependencies 301 between the different measurement parameters 211-217 are taken into account, wherein in each case the current values 563 for the different measurement parameters 211-217 are used for the computation.

A check is made during or subsequent to the calculation of the limit values 251 as to whether the current values of the measurement parameters have changed, 513, 514; if they have, a check is made as to whether a re-computation is necessary, 516. The check as to whether a re-computation is necessary can be based on the various parameter dependencies 301 for example. If for example the current value 563 of a measurement parameter 211-217 that is associated via a parameter dependency 301 with a measurement parameter 211-217 changes, for which previously the associated limit value 251 has been computed, then in 516 it can be determined that a re-computation is required. In this case previously computed limit values 251 are discarded, 517. The renewed selection of the different measurement parameters then occurs, 511.

When the computation for the current values 563 of the different measurement parameters 211-217 is successfully concluded, 513, 514, further limit values 251 for the selected measurement parameters 211-217 are computed 515, based on anticipated values 565. In this case, for example, currently non-active MR measurement sequences can be taken into account.

The order shown in FIG. 5 for the different steps is purely by way of example. Different orders can be implemented. It is not necessary for all steps to be carried out; for example the computation of the limit values 251 based on the anticipated values 565 in step 515 would be optional.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computer for planning a magnetic resonance measurement sequence, comprising:
   a user interface configured to receive inputs designating values of measurement parameters of a set of measurement parameters for a magnetic resonance measurement sequence;
   a processor in communication with said user interface, said processor being configured, for at least one selected measurement parameter among the respective measurement parameters for which values were entered as inputs via said user interface, to compute a limit value selected from the group consisting of a physiological limit value of a patient to be examined using the magnetic resonance measurement sequence, and a physical limit value of at least one component of a magnetic resonance data acquisition scanner that will be used to execute said magnetic resonance measurement sequence;
   a data interface configured to interface said processor with said magnetic resonance data acquisition scanner; and
   said processor being configured to generate control signals for operating said magnetic resonance data acquisition scanner, said control signals comprising values for said measurement parameters that are modified from the values entered via said user interface dependent on said limit value, and said processor being configured to provide said control signals to said data interface for transmission from said data interface to said magnetic data acquisition scanner.

2. The computer as claimed in claim 1 wherein said processor is configured to compute said limit value prospectively before entry of said values of measurement parameters via said user interface, and to then apply the prospectively computed limit value to the values of said measurement parameters entered via said user interface.

3. The computer as claimed in claim 1 wherein said processor is configured to compute said limit value from predetermined parameter dependencies between different measurement parameters of said set of measurement parameters and said at least one selected measurement parameter, and from values of different measurement parameters of said set of measurement parameters established via said user interface.

4. The computer as claimed in claim 3 wherein said processor is configured to establish a further limit value for said at least one selected measurement parameter from said predetermined parameter dependencies, and said at least one selected measurement parameter, and further based on anticipated values of said different measurement parameters of said set of measurement parameters, with said value of said different measurement parameters established by said user interface being at least partly different from said anticipated values.

5. The computer as claimed in claim 1 wherein said processor is configured to compute said limit value from an operator specification of said magnetic resonance data acquisition scanner.

6. The computer as claimed in claim 1 wherein said processor is configured to select said at least one selected measurement parameter from said set of measurement parameters dependent on a user action entered via said user interface, during a user interaction with said user interface.

7. The computer as claimed in claim 6 wherein said user action comprises selection of a logical grouping of measurement parameters in a graphical user interface of said user interface, said logical grouping comprising said at least one measurement parameter.

8. The computer as claimed in claim 6 wherein said user action comprises establishing values of a further measurement parameter of said set of measurement parameters by said user interaction.

9. The computer as claimed in claim 1 wherein said processor is configured is select said at least one selected measurement parameter from said set of measurement parameters dependent on a person profile selected from the group consisting of a person profile of the patient to be examined, and a person profile of a user of said user interface.

10. The computer as claimed in claim 1 wherein said processor is configured to select said at least one measurement parameter from said set of measurement parameters dependent on a computing power required for computation of said limit value.

11. The computer as claimed in claim 1 wherein said processor is configured to control said user interface on a first thread and is configured to compute said limit value of said at least one selected measurement parameter on a second thread, and wherein said processor is configured to execute said first thread with a higher priority than said second thread.

12. The computer as claimed in claim 1 wherein said processor is configured to activate said user interface to cause said user interface to present the computed limit value via the user interface during a user interaction with said user interface.

13. The computer as claimed in claim 1 comprising a memory, and wherein said processor is configured to store data designating said computed limit value in said memory, together with data designating values of the measurement parameters of the set of measurement parameters established via said inputs entered via said user interface.

14. The computer as claimed in claim 13 wherein said computer is configured to generate said data designating said values of said measurement parameters of said set of measurement parameters established by said user interaction as a range of dispersion sum of said values of said measurement parameters of said set of measurement parameters established by said user interaction.

15. The computer as claimed in claim 1 wherein said computer is configured to select said at least one selected measurement parameter from said set of measurement parameters in the group consisting of a measurement range in a readout direction of said magnetic resonance data acquisition scanner, a measurement range in a phase encoding direction of said magnetic resonance data acquisition scanner, a slice thickness of the patient to be examined, a repetition time of said sequence, an echo spacing said sequence, a spatial resolution in said readout direction, a spatial resolution in said phase encoding direction, a partial Fourier factor, an image acceleration factor for parallel imaging, a bandwidth for operating said magnetic resonance data acquisition scanner, a flow compensation mode for operating said magnetic resonance data acquisition scanner, a turbo factor for turbo spin echo imaging, a dimensionality of imaging with said sequence, a radio-frequency mode for use in said sequence, a number of concatenations to be generated in said sequence, and a number of slices of said patient to be examined with said sequence.

16. The computer as claimed in claim 15 wherein said computer is configured to determine said limit value from predetermined dependencies between respective measurement parameters in said set of measurement parameters, said predetermined parameter dependencies being selected from the group consisting of said measurement range in said readout direction, said spatial resolution in said readout direction, said echo spacing, said spatial resolution in said phase encoding direction, said partial Fourier factor, said image acceleration factor for parallel imaging, said turbo factor for turbo spin echo imaging, said repetition time, and said number of concatenations.

17. A magnetic resonance apparatus comprising:
a magnetic resonance data acquisition scanner;
a user interface configured to receive inputs designating values of measurement parameters of a set of measurement parameters for a magnetic resonance measurement sequence to be implemented by said scanner;
a processor in communication with said user interface, said processor being configured, for at least one selected measurement parameter among the respective measurement parameters for which values were entered as inputs via said user interface, to compute a limit value selected from the group consisting of a physiological limit value of a patient to be examined using the magnetic resonance measurement sequence, and a physical limit value of at least one component of the magnetic resonance data acquisition scanner that will be used to execute said magnetic resonance measurement sequence;
a data interface configured to interface said processor with said magnetic resonance data acquisition scanner; and
said processor being configured to generate control signals for operating said magnetic resonance data acquisition scanner, said control signals comprising values for said measurement parameters that are modified from the values entered via said user interface dependent on said limit value, and said processor being configured to provide said control signals to said data interface for transmission from said data interface to said magnetic data acquisition scanner.

18. A method for planning a measurement by execution of a magnetic resonance measurement sequence by a magnetic resonance data acquisition scanner, said method comprising:
providing inputs to a processor via a user interface configured to receive said inputs designating measurement parameters of a set of measurement parameters for a magnetic resonance measurement sequence;
in said processor, for at least one selected measurement parameter among the respective measurement parameters for which values were entered as inputs via said user interface, computing a limit value selected from the group consisting of a physiological limit value of a patient to be examined using the magnetic resonance measurement sequence, and a physical limit value of at least one component of a magnetic resonance data acquisition scanner that will be used to execute said magnetic resonance measurement sequence;
interfacing said processor with said magnetic resonance data acquisition scanner; and
in said processor, generating control signals for operating said magnetic resonance data acquisition scanner, said control signals comprising values for said measurement parameters that are modified from the values entered via said user interface dependent on said limit value, and providing said control signals from said processor to said magnetic data acquisition scanner.

* * * * *